United States Patent [19]

Bernstein et al.

[11] Patent Number: 4,860,741

[45] Date of Patent: Aug. 29, 1989

[54] MODULAR INHALATION TOWER FOR LABORATORY ANIMALS

[75] Inventors: David M. Bernstein, Geneva; Hermut Fleissner, Bernex, both of Switzerland

[73] Assignee: Research & Consulting Co. A.G., Switzerland

[21] Appl. No.: 141,255

[22] Filed: Jan. 6, 1988

[30] Foreign Application Priority Data

Feb. 9, 1987 [CH] Switzerland .......................... 475/87

[51] Int. Cl.[4] .............................................. A61M 16/00

[52] U.S. Cl. ................................ 128/204.18; 119/15; 119/52.1

[58] Field of Search ..................... 128/204.18; 119/15, 119/17, 52 R, 1

[56] References Cited

U.S. PATENT DOCUMENTS 3,548,840 12/1970 Baumgartner ........................ 119/17

4,721,060 1/1988 Cannon et al. ........................ 119/15

FOREIGN PATENT DOCUMENTS 1014543 4/1983 U.S.S.R. .

OTHER PUBLICATIONS

"The Battelle Nose-Only, Flow Past Inhalation Toxicology Exposure System", 1976, by Battelle Centres de recherche de Genève.

"The Flow-Past Chamber: An Improved Nose-Only Exposure System for Rodents", by Cannon et al., 1983.

*Primary Examiner*—Edgar S. Burr

*Assistant Examiner*—Aaron J. Lewis

*Attorney, Agent, or Firm*—Cushman, Darby & Cushman

[57] ABSTRACT

An inhalation tower comprises two columns forming two concentric ducts each made up of segments fitted into one another. The segments forming the outer duct have an external annular portion at one end and an internal annular portion at the other end, the axial height of the latter being less than the height of the external annular portion, so as to leave a space for receiving a plate. The internal duct has radial connecting ducts which open into the end of a cylindrical cavity formed in the external segment, a space being reserved between the connecting duct and the diameter of an opening through the end of the cavity. The cavity is adapted to receive an inhalation chamber borne by the tray.

5 Claims, 1 Drawing Sheet

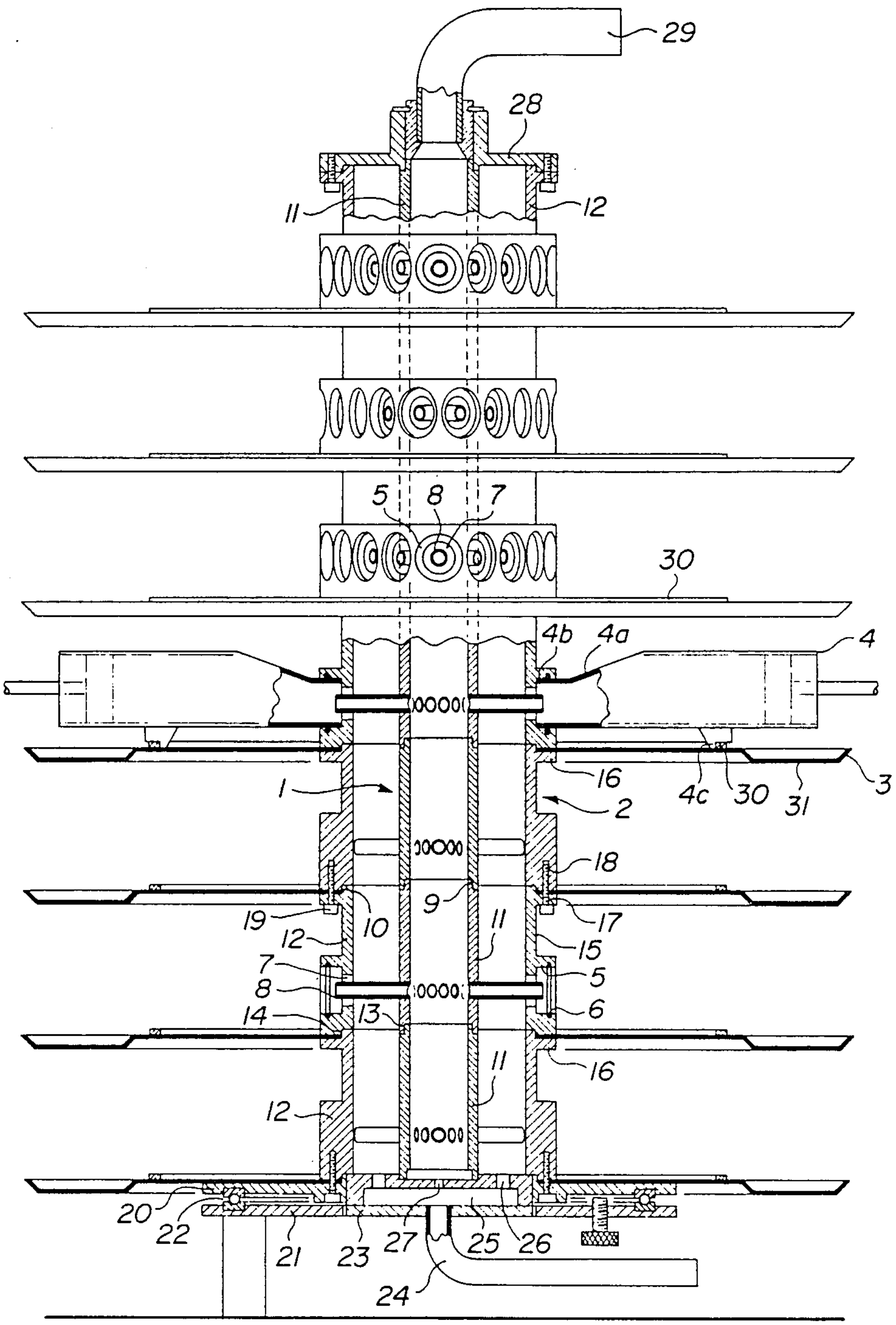
29
28
11
12
5
8
7
30
4b
4a
4
16
4c
30
31
3
1
2
18
9
10
19
17
12
11
15
7
5
8
6
14
13
16
11
12
20
22
21
23
27
25
26
24

MODULAR INHALATION TOWER FOR LABORATORY ANIMALS

BACKGROUND OF THE INVENTION

The invention relates to a modular inhalation tower for laboratory animals comprising two concentric vertical ducts around the vertical axis of the tower, which has a number of tiers, each of which comprises a tray for supporting individual inhalation chambers and radial connecting ducts, grouped in tiers and distributed at equal angles on each tier, in order to connect each inhalation chamber to the central internal distribution duct, the central external duct for evacuating the inhaled gas is formed with openings concentric with each connecting duct in order to connect each inhalation chamber with the central external evacuation duct.

The aim of these towers, in which animals are imprisoned in individual chambers, is to limit the distribution of aerosol to the respiratory tracts and to distribute a measured quantity of aerosol to the lungs. Inhalation devices based on this principle are described in an article by W.C. Cannon, E.F. Blantore and K.E. McDonald of Pacific Northwest Laboratories of Battelle Memorial Institute, in American Industrial Hygiene Association Journal, Volume 44, pages 923–928 (December 1983).

In the inhalation device described in this article, the aerosol is continuously distributed through a small tube to the nose of each animal and is inhaled on leaving the tube without being in contact with other parts of the animal's body or with other animals. Construction of a modular inhalation tower comprising a supporting tray at each tier was proposed in a technical memorandum published in Spring 1986 by the Geneva Research Centre of Battelle Memorial Institute.

OBJECTS OF THE INVENTION

The aim of the invention is specifically to construct an aforementioned modular inhalation tower, which has a very high capacity and minimum bulk. The inhalation tower proposed in the aforementioned technical memo was made of PVC, and consequently the increase in capacity creates problems of heating and consequently of evacuating the heat, which necessitated use of a metal for improved evacuation of heat by simple convection with the ambient air. This change in material resulted in modifications in the embodiment of the cooling tower.

SUMMARY OF THE INVENTION

According to the present invention, there is provided a modular inhalation tower for laboratory animals, the tower comprising a plurality of tiers stackable one on top of another, and a plurality of trays for supporting one or more laboratory animal, wherein each tier has means for supplying gas to the laboratory animal(s) and for evacuating exhaled gas, wherein each tier has complementary formations formed on opposite ends thereof, which complementary formations are configured to enable stacked tiers to locate and engage with one another, the complementary formations also being configured at the periphery of the ends of the tiers so that one of the trays can be received between adjacent stacked tiers.

The single accompanying drawing is a diagrammatic view in elevation, partly in section, of an embodiment of the inhalation tower, by way of example.

DETAILED DESCRIPTION OF THE DRAWINGS

The inhalation tower comprises two coaxial vertical ducts 1, 2 forming a column bearing a number of circular trays 3 regularly spaced and each defining a tier adapted to receive individual inhalation enclosures 4. The enclosures are substantially tubular in shape and terminate in a front part in the form of a truncated rectangular cone 4a terminating in a cylindrical end 4b adapted to engage in a recess 5 formed in the wall of the external duct 2, an O-ring seal 6 being disposed in a groove in the cylindrical wall of recess 5. The end of recess 5 is formed with an aperture 7 which connects it to the interior of the external duct 2 and leaves room at its centre for a distribution pipe 8 screwed into the wall of the internal duct 1.

The internal duct 1 and the external duct 2 making up the column are each formed of fitted-together segments 11, 12 rspectively, the width of the segments corresponding to the height of a tier in the installation tower. To this end, the front end of each segment 11, 12 comprises external annular parts 9, 10 respectively whereas the bottom ends of the segments 11, 12 comprise internal annular parts 13, 14 respectively. The respective diameters of parts 9 and 10 are complementary to the respective diameters of the internal portions, so that the bottom ends of the respective segments 11, 12 can fit on to the top ends of the respective adjacent segments. Furthermore, the height of the internal portion 14 of the external segment 12 is less than the height of the external portion 10 of the same segment, resulting in an annular space adapted to receive the inner edge of the circular tray 3.

The outer surface of the external duct 2 has an annular recess 15 which extends between the tier of recesses 5 and the outer portion 10, thus forming an annular projection 16 adjacent the external portion 10. Four equidistant apertures 17 are formed perpendicular to the plane of the annular projection 16. They correspond to four threads 18 formed perpendicular to the plane of the opposite end surface of the same segment 12. An angular offset corresponding to a half-step separating the recesses 5 exists between the apertures 17 extending through the annular projection 16 and the threads 18 formed at the other end, so that the rows of successive recesses are offset from one another by half a pitch. The circular trays 3 also comprise four equidistant holes for corresponding to the apertures 17 and threads 18. A screw 19 is inserted into each thread 18 through the respective apertures 17 and the holes in the circular plate 3, so that all the segments 2 and trays 3 are secured to one another along the entire height of the inhalation tower.

The tower rests on a disk 20 mounted on a bearing frame 21 via a ball bearing 22. Disk 20 is secured at its centre to a smaller-diameter disk 23 which fits on to a central opening of the bearing frame 21. A supply duct 24 is mounted for rotation at the centre of disk 23. A closed space is formed between the two disks 20 and 23. Space 25 communicates with the collector of gas inhaled by the animals, formed between the internal duct 1 and the external duct 2 by orifices 26 formed through the disk 20. A smaller-diameter orifice 27 extends through the centre of disk 20 and is for completely discharging the water during cleaning thereof.

At the top end, the central column is closed by a cover plate 28 which is adjusted to fit the external segment 12 and internal segment 11 and bears a supply tube 29 mounted for rotation at its centre. Tube 29 is for connecting to a source of gas or aerosol to be inhaled. Since the cover plate is fitted on to the ends of the two segments 11 and 12, the gas or aerosol coming from tube 29 is introduced into the internal duct 1.

Each tray has a circular rib 30 for radially positioning the inhalation chambers 4, each of which comprises a pair of projections 4c for engaging inside the circular rib 30. Outside the rib 30, plate 3 comprises an annular channel 31 for collecting the urine and faeces of the animals.

As shown on the drawing, when an animal is housed in an inhalation chamber 4 and its front end is inserted into a recess 5, the animal's nose is in the immediate neighbourhood of the end of the distribution pipe 8, which delivers the gas or aerosol to be inhaled. The air breathed out by the animal can escape via the annular aperture 7, which opens into the annular evacuation space formed between the internal duct 1 and the external duct 2.

The inhalation tower which has been described has numerous advantages. It has a high capacity in dependence on volume, and its modular construction enables the height of the tower to be adapted to requirements. The modular design is also very advantageous in cleaning. The heat released by the tens of animals which the tower can hold, can be discharged by natural convection between ambient air and the metal parts of the tower. The rotary mounting of the tower on its support also saves space, in that it is not necessary to have access to the tower over its entire periphery but only over a part of the periphery.

We claim:

1. A modular inhalation tower for laboratory animals comprising two concentric vertical ducts defining a central external evacuation duct and a central internal distribution duct around the vertical axis of the tower, which has a number of tiers, each of which comprises a tray for supporting individual inhalation chambers and radial connecting ducts grouped in tiers and distributed at equal angles on each tier, in order to connect each inhalation chamber to the central internal distribution duct, the central external duct for evacuating the inhaled gas being formed with openings concentric with each connecting duct in order to connect each inhalation chamber to the central external evaluation duct, wherein each duct is divided into segments each corresponding to a tier, each segment ending in surfaces shaped so as to fit into complementary surfaces of adjacent segments, the complementary surfaces of adjacent segments, the complementary surfaces of the segment forming the central external duct comprising, firstly, an external annular portion and, secondly, and internal annular portion of complementary diameter, the axial height of the internal annular portion is less than that of the external annular portion by a value corresponding of the thickness of one of the trays so as to define an annular space for receiving a tray between each pair of adjacent segments, a cylindrical annular rcess being formed in the outer surface of each segment of the central external duct between two projecting annular parts extending from the two respective ends of the duct segment, one of the projecting annular parts being formed with holes parallel to the duct axis and distributed at equal angles around the axis and the other annular part having threads parallel to the duct axis and equal in number to thè holes and distributed at equal angles, the threads being adapted to receive screws guided through the corresponding holes in the annular part of the adjacent duct segment and the tray disposed in the annular space.

2. An inhalation tower according to claim 1, characterized in that the openings are concentric with each connecting duct formed through the central external duct and are in one of the annular parts and aperture opens concentricaly into a cylindrical cavity having a side wall formed with a annular recess for receiving an O-ring seal, the cylindrical cavity receiving the front end of an individual inhalation chamber.

3. An inhalation tower according to claim 1, characterised in that the holes are distributed at equal angles across one of the projecting annular parts and the threads in the other annular part distributed at equal angles and in number equal to the holes, are offset at an angle to the holes in the same duct segment by a value corresponding to an angular half-pitch of the apertures.

4. An inhalation tower according to claim 1, characterised in that it rests on a frame via bearing concentric with the vertical ducts.

5. An inhalation tower according to claim 1, characterised in that each tray has peripheral annular channel for collecting the urin from the animals.

* * * * *